United States Patent
Adams et al.

(10) Patent No.: US 6,653,353 B2
(45) Date of Patent: Nov. 25, 2003

(54) COSMETIC AND PERSONAL CARE COMPOSITIONS

(75) Inventors: Gerald Adams, Wirral (GB); Ezat Khoshdel, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/097,031

(22) Filed: Mar. 13, 2002

(65) Prior Publication Data

US 2002/0176834 A1 Nov. 28, 2002

(30) Foreign Application Priority Data

Mar. 15, 2001 (GB) .............................. 0106467

(51) Int. Cl.$^7$ ...................... A51K 31/03; A51K 31/035; A51K 31/025; A51K 31/04
(52) U.S. Cl. ...................... 514/749; 514/746; 514/759; 514/740; 514/741
(58) Field of Search .............................. 514/741, 740, 514/746, 749, 759

(56) References Cited

U.S. PATENT DOCUMENTS 3,993,745 A  11/1976  Cella et al.

FOREIGN PATENT DOCUMENTS

| DE | 198 05 432 C1 | 3/1999 |
| EP | 0943312 A2 | 9/1999 |

OTHER PUBLICATIONS

Search Report Under Section 17 Application No. GB 0106467.4 dated Aug. 29, 2001.

*Primary Examiner*—Theodore J. Criares
*Assistant Examiner*—S. Jiang
(74) *Attorney, Agent, or Firm*—Michael P. Aronson

(57) ABSTRACT

Cosmetic or personal care compositions comprise: a hair styling polymer having one or more groups selected from acidic functional groups, anionic groups derived from the acidic functional groups or a mixture of said groups; a partially or fully fluorinated compound having one or more groups selected from amino groups, acid salts of the amino groups or a mixture of said groups, wherein the partially or fully fluorinated compound comprises an aromatic ring; and a cosmetically acceptable diluent or carrier. The compositions are particularly effective under high humidity conditions.

18 Claims, No Drawings

COSMETIC AND PERSONAL CARE COMPOSITIONS

FIELD OF THE INVENTION

This invention relates to cosmetic and personal care compositions, a method of treating hair with the compositions and the use of the compositions for the cosmetic treatment of hair.

BACKGROUND AND PRIOR ART

The desire to have the hair retain a particular shape or style is widely held. The most common approach for accomplishing styling of hair is the application of a composition to dampened hair, after shampooing and/or conditioning, or to dry, styled hair. These compositions provide temporary styling benefits and can readily be removed by water or shampooing. To date, the materials employed in hair care compositions to provide styling benefits have generally been natural or synthetic resins and have been applied in the form of, for example, sprays, mousses, gels and lotions.

Recently, it has become desirable to have a high level of style retention, or strong hold, delivered from a hair spray composition. In a typical hair spray, hold is achieved by the use of commercially available styling polymers, such as AMPHOMER(™), supplied by National Starch Chemical Company, LUVIMER(™), supplied by BASF, GANTREZ (™), supplied by ISP Chemicals and also silicone graft copolymers, supplied by Mitsubishi Chemicals.

Typically, the styling polymers have a carbon backbone comprising various hydrophilic and hydrophobic vinylic monomers. These polymers can be nonionic or they can carry a charge, usually a negative charge. The hydrophilic monomer is employed to render the polymer water-soluble and the hydrophobic monomer is generally selected to enhance humidity resistance of the styling resins.

It is known that compositions containing certain known hair styling polymers can perform poorly under conditions of high humidity. Thus, hair styled with these compositions can lose its shape and any other benefits conferred by the compositions when the ambient humidity increases or the hair and/or the scalp becomes damp.

Traditionally, the anionically charged hair styling resins are formed from the corresponding acids (neutralised) using alkalising agents.

The alkalising or neutralising agents are usually an inorganic base such as sodium, potassium and ammonium hydroxide and/or an organic base. The organic bases commonly employed in a cosmetic formulation are alkyl and/or hydroxyalkyl, primary, secondary and tertiary amines. Examples of such materials employed in the formulations are 2-amino-2-methyl-1,3-propanediol (AMPD), 2-amino-2-ethyl-1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA) and dimethyl stearamine (DMS). Indeed even higher alkyl chain amines containing 12 or 16 carbons have been employed to combat humidity but without much success.

Although the common neutralising agents described above help to improve the film properties of the styling resin, they do not perform well under high humidity conditions.

DE 19805432 C describes a hair styling formulation containing a polymer with acid groups at least partly neutralised with fluorinated amine. The fluorinated amine is preferably a primary or secondary amine which contains at least one specified linear fluoroalk(en)yl group and optionally a specified linear alkyl group or hydrogen. The formulation is said to provide a flexible hydrophobic film without impairing spraying.

EP 0943312 A discloses a hair treatment composition containing a complex formed from at least one fluorinated acid and at least one polymer with basic groups or a complex of a salt of a fluorinated acid and a polymer with protonated or quaternized amine groups. The composition also contains at least one film-forming, hair-fixing polymer. These compositions are said to deposit a reduced amount of residue on the hair without reducing the hair-fixing performance.

U.S. Pat. No. 3,993,745 relates to hair treatment compositions comprising specified hydrophobic-lipophilic perfluorinated compounds and, optionally, hair styling resins. These compositions are said to substantially reduce the excess flow of the sebum or sebaceous secretions and there is no mention of the perfluorinated compounds acting as neutralising agents.

There is no mention in any of the above documents of the use of fluorinated amine compounds that contain an aromatic ring as neutralising agents in hair styling compositions.

Surprisingly, it has been found that the use of certain fluoroamines significantly improves the holding power of styling resins under high humidity conditions.

It is an aim of the present invention to provide cosmetic and personal care compositions comprising a hair styling polymer in which the film forming properties of the hair styling polymer are improved, particularly under high humidity conditions.

It is a further aim of the present invention to provide other advantages in cosmetic and personal care compositions. For example, compositions of the invention may, surprisingly, have one or more advantageous properties selected from low tack polymer film characteristics, and when applied to hair can give improved hold of hair and/or enhanced shine of hair and/or better natural movement of hair.

SUMMARY OF THE INVENTION

According to the present invention, there is provided a cosmetic or personal care composition comprising: a hair styling polymer having one or more groups selected from acidic functional groups, anionic groups derived from the acidic functional groups or a mixture of said groups; a partially or fully fluorinated compound having one or more groups selected from amino groups, acid salts of the amino groups or a mixture of said groups, wherein the partially or fully fluorinated compound comprises an aromatic ring; and a cosmetically acceptable diluent or carrier.

In another aspect, the invention provides a method of treating hair using a composition of the invention.

In yet another aspect, the invention provides the use of a composition of the invention in the cosmetic treatment of hair.

DETAILED DESCRIPTION OF THE INVENTION

Partially or Fully Fluorinated Compound

The compositions of the present invention comprise a partially or fully fluorinated compound having one or more amino groups and at least one aromatic ring. In the compositions, the compound may have the amino group in the form of a free amine, as an acid salt or as a mixture of free amine and acid salt.

Preferably, the partially or fully fluorinated compound has the formula $RNR^1R^2$, wherein R is a partially or fully fluorinated group selected from aryl, aralkyl, heteroaryl or heteroaralkyl groups and $R^1$ and $R^2$ are independently selected from alkyl having 1 to 12 carbon atoms, aryl, aralkyl, heteroaryl or heteroaralkyl groups which are optionally fluorinated, or H.

It is particularly preferred that $R^1$ and $R^2$ are H. It is also preferred that R is a phenyl group substituted on the ring with one or more groups selected from fluorine and partially or fully fluorinated $C_1$ to $C_6$ alkyl (eg, trifluoromethyl) and optionally substituted by one or more other substituents.

Optionally, two of R, $R^1$ and $R^2$ may be linked together to form a four, five, six or seven membered heterocyclic ring containing nitrogen and at least one other heteroatom selected from nitrogen, oxygen or sulfur, preferably nitrogen. The heterocyclic ring may be fused to a phenyl group or further heterocyclic ring wherein the further heterocyclic ring contains at least one of the heteroatoms selected from nitrogen, oxygen and sulfur and is partially or fully unsaturated.

The term "alkyl" as used herein, includes straight chain and, for alkyl groups containing three or more carbon atoms, branched and also cycloalkyl groups. The cycloalkyl groups may optionally contain a heteroatom selected from nitrogen, oxygen and sulfur. Examples of straight chain alkyl include methyl, ethyl, propyl, butyl, pentyl and hexyl. Examples of branched alkyl include isopropyl, isobutyl, and tert-butyl. Examples of cycloalkyl groups include cyclopropyl, cyclobutyl, cyclopentyl and cyclohexyl.

The alkyl groups may optionally be substituted with, for example, aryl, aralkyl and heteroaryl groups as defined below and/or one or more groups such as, for example, amino, fluorine, chlorine, bromine, iodine, nitro, phenyl, hydroxy, sulfide, thiol, ester (ie, —$CO_2$—$R^3$ where $R^3$ is selected from: $C_{1-6}$ unsubstituted alkyl, alkenyl or alkynyl; and aralkyl, aryl, heteroaryl or heteroaralkyl as defined herein), and amide (ie, —$CONR^4R^5$ where $R^4$ and $R^5$ are independently selected from: hydrogen; $C_{1-6}$ unsubstituted alkyl, alkenyl or alkynyl; and aryl, aralkyl, heteroaryl and heteroaralkyl groups as defined herein). Alkyl groups may be substituted in the alkyl chain by one or more heteroatoms selected from O, S and NH.

The terms "alkenyl" and "alkynyl" are defined similarly to the term "alkyl" but the groups contain one or more carbon—carbon double or triple bonds, respectively.

The term "aryl" as used herein includes phenyl and other polycyclic fused ring compounds which contain at least one fully aromatic ring, such as, for example, naphthalene and 3,4-dihydronaphthalene, optionally substituted with one or more groups such as, for example, amino, fluorine, chlorine, bromine, iodine, nitro, phenyl, hydroxy, sulfide, thiol, ester (ie, —$CO_2$—$R^3$ where $R^3$ is selected from: $C_{1-6}$ unsubstituted alkyl, alkenyl or alkynyl; and aralkyl as defined herein), and amide (ie, —$CONR^4R^5$ where $R^4$ and $R^5$ are independently selected from: hydrogen; $C_{1-6}$ unsubstituted alkyl, alkenyl or alkynyl; and aralkyl, groups as defined herein).

The term "aralkyl" as used herein refers to $C_1$ to $C_6$ alkyl substituted with aryl (eg, benzyl).

The term "heteroaryl" as used herein refers to monocyclic and polycyclic fused or non-fused ring containing compounds containing at least one heteroatom such as, for example, nitrogen, sulfur or oxygen or mixtures thereof within any of the rings and where at least one of the rings is aromatic. The ring or rings comprising the heteroatom may be three, four, five, six, seven or eight membered. The term "heteroaryl" is intended to include compounds that comprise partially or fully saturated rings, in addition to aromatic rings. The heteroatom may be situated in the partially or fully saturated rings or in the aromatic ring.

Non-limiting examples of such heteroaryl compounds include aryl-substituted piperazines, azo compounds, pyrazoles, thiazoles, oxazoles, 1,2,4-triazoles, benzothiazoles, benzotriazoles, pyrimidines, thiadiazines, pyridines, thiophenes, azepines, carbazoles, quinolines and iso-quinolines.

The term "heteroaralkyl" as used herein refers to $C_1$ to $C_6$ alkyl substituted with heteroaryl (eg, pyrazolylmethyl).

The heteroaryl compounds may optionally be substituted with alkyl, alkaryl or aryl groups as defined above or with one or more other groups selected from, for example, amino, fluorine, chlorine, bromine, iodine, nitro, phenyl, hydroxy, sulfide, thiol, ester (ie, —$CO_2$—$R^3$ where $R^3$ is selected from: $C_{1-6}$ unsubstituted alkyl, alkenyl or alkynyl; and aralkyl as defined herein), and amide (ie, —$CONR^4R^5$ where $R^4$ and $R^5$ are independently selected from: hydrogen; $C_{1-6}$ unsubstituted alkyl, alkenyl or alkynyl; and aralkyl, groups as defined herein).

The compounds contain one or more fluorine atoms, preferably at least three fluorine atoms. The fluorine atoms may replace any one of the hydrogen atoms bound to carbon atoms in the corresponding unfluorinated compound.

Fluorinated amines which are suitable for use in the present invention are commercially available. The compounds may be obtained by fluorination of amines or by the formation of an amino group in an already fluorinated compound, by conventional methods well-known to those skilled in the art.

Non-limiting examples of fluoroamines suitable for use in compositions of the present invention include 4-(trifluoromethyl)aniline, 2,3,5,6-tetrafluoro-4-(trifluoromethyl)aniline, (1-(2,5-dichloro-phenyl)-ethylidene)-(2-trifluoromethyl-phenyl)-amine, (1-(4-chloro-phenyl)-propylidene)-(2-trifluoromethyl-phenyl)-amine, (1-benzotriazol-1-yl-butyl)-(2-chloro-4-fluoro-phenyl)-amine, (1-benzotriazol-1-yl-butyl)-(3,4-difluoro-phenyl)-amine, (1-benzotriazol-1-yl-butyl)-(3,5-bis-trifluoromethyl-phenyl)-amine, (1-benzotriazol-1-yl-butyl)-(4-trifluoromethyl-phenyl)-amine, (1-naphthalen-1-yl-ethyl)-(2,2,2-trifluoro-1-phenyl-ethylidene)-amine, (1-pyridin-2-yl-ethylidene)-(2-trifluoromethyl-phenyl)-amine, (1-pyridin-3-yl-ethylidene)-(2-trifluoromethyl-phenyl)-amine, (1-pyridin-4-yl-ethylidene)-(2-trifluoromethyl-phenyl)-amine, (1-thiophen-2-yl-ethylidene)-(2-trifluoromethyl-phenyl)-amine, (2,6-dinitro-4-trifluoromethyl-phenyl)-dipropyl-amine, (2-(3,4-dimethoxy-phenyl)-ethyl)-(4-fluoro-benzylidene)-amine, (2-benzyloxy-benzylidene)-(4-fluoro-phenyl)-amine, (2-bromo-4,6-difluoro-phenyl)-isoquinolin-1-yl-amine, (2-chloro-5-nitro-benzylidene)-(3-fluoro-4-methyl-phenyl)-amine, (2-chloro-phenyl)-(4-(2-fluoro-4-methoxy-phenyl)-5-methyl-thiazol-2-yl)-amine, (2-difluoromethoxy-5-nitro-benzylidene)-(1,2,4)triazol-4-yl-amine, (2-difluoromethoxy-5-nitro-benzylidene)-(2-methoxy-phenyl)-amine, (2-difluoromethoxy-5-nitro-benzylidene)-(3-nitro-phenyl)-amine, (2-difluoromethoxy-5-nitro-benzylidene)-(3-trifluoromethyl-phenyl)-amine, (2-difluoromethoxy-5-nitro-benzylidene)-(4-difluoromethoxy-phenyl)-amine, (2-difluoromethoxy-5-nitro-benzylidene)-(4-fluoro-phenyl)-amine, (2-difluoromethoxy-5-nitro-benzylidene)-(4-iodo-phenyl)- amine, (2-difluoromethoxy-5-nitro-benzylidene)-(4-methoxy-phenyl)-amine, (2-difluoromethoxy-5-nitro-benzylidene)-(4-trifluoromethoxy-phenyl)-amine, (2-difluoromethoxy-5-nitro-benzylidene)-(5-methyl-2-phenyl-2H-pyrazol-3-yl)-amine, (2-difluoromethoxy-5-nitro-benzylidene)-(5-methyl-2H-pyrazol-3-yl)-amine, (2-difluoromethoxy-5-nitro-benzylidene)-naphthalen-1-yl-amine, (2-fluoro-benzylidene)-(4-p-tolyl-piperazin-1-yl)-amine (2-fluoro-benzylidene)-(4-pyridin-2-yl-piperazin-1-yl)-amine, (3,4-dichloro-phenyl)-(4-fluoro-benzylidene)-amine, (3,4-dihydro-2H-naphthalen-1-ylidene)-(2-trifluoromethyl-phenyl)-amine, (3,5-dichloro-phenyl)-(4-fluoro-benzylidene)-amine, (3-(4-fluoro-phenyl)-1-phenyl-1H-pyrazol-4-ylmethylene)-(4-methoxy-phenyl)-amine, (3-(4-fluoro-phenyl)-1-phenyl-1H-pyrazol-4-ylmethylene)-p-tolyl-amine, (3-(4-fluoro-phenyl)-1-phenyl-1H-pyrazol-4-ylmethylene)-phenyl-amine, (3-chloro-phenyl)-(2-difluoromethoxy-5-nitro-benzylidene)-amine, (3-fluoro-4-methyl-phenyl)-(1H-indol-3-ylmethylene)-amine, (3-nitro-benzylidene)-(5-trifluoromethyl-benzothiazol-2-yl)-amine, (4-(2-chloro-benzyl)-piperazin-1-yl)-(2-trifluoromethyl-benzylidene)-amine, (4-(2-chloro-benzyl)-piperazin-1-yl)-(4-fluoro-benzylidene)-amine, (4-(4-chloro-phenyl)-piperazin-1-yl)-(2-fluoro-benzylidene)-amine, (4-fluoro-benzylidene)-(4-p-tolyl-piperazin-1-yl)-amine, (4-fluoro-benzylidene)-naphthalen-2-yl-amine, (4-fluoro-benzylidene)-pyridin-2-yl-amine, (4-p-tolyl-piperazin-1-yl)-(2-trifluoromethyl-benzylidene)-amine, (4-tert-butyl-6-trifluoro-methyl-pyrimidin-2-yl)-(2,6-dinitro-4-trifluoromethyl-phenyl)-amine, (5-chloro-pyridin-2-yl)-(4-fluoro-benzylidene)-amine, (6-methoxy-3,4-dihydro-2H-naphthalen-1-ylidene)-(2-trifluoromethyl-phenyl)-amine, (9-ethyl-9H-carbazol-3-ylmethylene)-(3-fluoro-4-methyl-phenyl)-amine, (bis-(4-trifluoromethyl-phenyl)-methylene)-trityl-amine, 3,5-dimethyl-n-(4-(trifluoromethyl)benzylidene)-4H-1,2,4-triazol-4-amine, (2,4-bis(difluoromethoxy)phenyl)-1,3-thiazol-2-amine, (3-nitrophenyl)-n-(3-(trifluoromethyl)phenyl)-1,3-thiazol-2-amine, 4-(4-ethoxyphenyl)-n-(3-(trifluoromethyl)phenyl)-1,3-thiazol-2-amine, (4-fluorophenyl)-n-(3-(trifluoromethyl)phenyl)-1,3-thiazol-2-amine, (4-methylphenyl)-n-(3-(trifluoromethyl)phenyl)-1,3-thiazol-2-amine, 4-(4-nitrophenyl)-n-(3-(trifluoromethyl)phenyl)-1,3-thiazol-2-amine, phenyl-n-(3-(trifluoromethyl)phenyl)-1,3-thiazol-2-amine, (4-fluorophenyl)-n-(3-methoxybenzylidene)-4H-1,3,4-thiadiazin-2-amine, benzo(H)isoquinolin-4-yl-(4-fluoro-benzylidene)-amine, benzotriazol-1-ylmethyl-(2,3,4-trifluoro-phenyl)-amine, benzotriazol-1-ylmethyl-(2,5-difluoro-phenyl)-amine, benzotriazol-1-ylmethyl-(4-fluoro-3-nitro-phenyl)-amine, benzyl-(2,3,4,5,6-pentafluoro-benzylidene)-amine, biphenyl-4-yl-(2-difluoromethoxy-5-nitro-benzylidene)-amine, carbazol-9-yl-(2-difluoromethoxy-benzylidene)-amine, carbazol-9-yl-(4-difluoromethoxy-benzylidene)-amine, ethyl-(2-nitro-4-trifluoromethyl-phenyl)-amine, n-(2-(difluoromethoxy)-5-nitrobenzylidene)-2-methyl-1,3-oxazol-5-amine, n-(3-fluorobenzylidene)-3,5-dimethyl-4H-1,2,4-triazol-4-amine, n-(4-((difluoromethyl)thio)phenyl)-3,4,5,6-tetrahydro-2H-azepin-7-amine, n-(4-(2-methoxyphenyl)-1-piperazinyl)-n-(2-(trifluoromethyl)benzylidene)amine, n-(4-(difluoromethoxy)phenyl)-3,4,5,6-tetrahydro-2H-azepin-7-amine, n-(4-fluorobenzylidene)-3,5-dimethyl-4H-1,2,4-triazol-4-amine, n-(5-bromo-2-fluorobenzylidene)-3,5-dimethyl-4H-1,2,4-triazol-4-amine, n-benzyl-2-(4-fluorophenyl)-4-((4-methylphenyl)sulfonyl)-1,3-oxazol-5-amine, and n-phenyl-3-(trifluoromethyl)(1,2,4)triazolo(3,4-b)(1,3,4)thiadiazol-6-amine.

The amines may be included in the compositions as free amines, as acid addition salts (eg, hydrochlorides or hydrobromides) or as mixtures of free amines and acid salts.

Preferably, the partially or fully fluorinated compound is selected from the group consisting of: 2,3,5,6-tetrafluoro-4(trifluoromethyl)aniline; 4-(trifluoromethyl)aniline and mixtures thereof.

In addition, compositions according to the present invention may optionally further comprise a non-fluorinated amine.

The non-fluorinated amine is preferably an amine conventionally used in cosmetic and personal care compositions. Preferably, the amine is selected from the group consisting of 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethylstearamine (DMS) and mixtures thereof.

A long chain amine neutralising agent such as stearamidopropyl dimethylamine or lauramidopropyl dimethylamine may be employed in the compositions, as is described in U.S. Pat. No. 4,874,604.

The compositions of the present invention may further comprise an inorganic base. The inorganic base is preferably selected from the group consisting of sodium hydroxide, potassium hydroxide, ammonium hydroxide, borax and mixtures thereof.

The ratio of partially or fully fluorinated compound to non-fluorinated amine by weight in the compositions of the invention may be in the range of from 10:1 to 1:10, preferably from 5:1 to 1:5, more preferably from 2:1 to 1:2.

In a preferred composition, the ratio of inorganic base to partially or fully fluorinated compound and non-fluorinated amine by weight is in the range of from 100:1 to 1:100.

The degree of neutralisation of the hair styling polymer in the compositions of the present invention ranges from 10% to 100%, preferably from 50% to 99%, more preferably from 90% to 98%.

The degree of neutralisation and the choice and the ratio of inorganic versus organic base depend on the nature of the styling resin as well as the formulation. The amount in grams of base ($W_B$) required to neutralise any given styling resin can be deduced from calculations which takes into account the acid value of the polymer (A), the amount of polymer ($W_P$), molecular weight of the base ($M_B$), molecular weight of the acidic moiety ($M_A$) and the degree of neutralisation (N) as shown below.

$$W_B = W_P \times A/100 \times 1/M_A \times M_B \times N$$

The acid value (A) can be experimentally determined by, for example, titrating a known amount of the polymer with base or theoretically by considering the original acidic content of the styling resin. For example, a styling resin with 30% of the carboxylic acid containing monomer will have an acid value of 30.

Amounts of the partially or fully fluorinated compound in the compositions of the invention range from 0.001% to 10% by weight of the total composition, preferably from 0.01% to 5%, more preferably from 0.1% to 0.7% by weight of the total composition.

Hair Styling Polymer

The compositions of the present invention comprise a hair styling polymer having acidic functional groups, anionic groups derived from the acidic functional groups or a mixture of said groups.

Particularly preferred hair styling polymers for use in the compositions of the invention comprise carboxylic acid groups and/or salts thereof.

The compositions of the invention preferably comprise from 0.01% to 10% by weight (of the total composition), more preferably from 0.1% to 10% by weight, of the hair styling polymer. The amount of the polymer may, for example, range from 0.5% to 10%, preferably 0.75% to 6% by weight based on total weight of the composition.

The compositions of the invention preferably retain a degree of bond strength (where the bond strength is determined by the method described herein in the examples in the section under the heading "Method for determining bond strengths") at relatively high temperatures and high humidity, in order that the styling composition can continue to be effective at styling hair under these conditions. Therefore, the compositions preferably have a bond strength of at least 15 g (more preferably at least 25 g), such as 15 g to 80 g or 25 g to 70 g, for example, at 20° C. and 80% relative humidity.

Hair styling polymers are used, for example, in hair styling compositions such as hair sprays, gels, and mousses. Hair styling polymers are well known articles of commerce and many such polymers are available commercially which contain moieties which render the polymers anionic. Such anionic polymers are generally made anionic by neutralisation of an acid form of the polymer and are suitable for use in the compositions of the invention. Suitable hair styling polymers include, for example, block and graft copolymers. The polymers may be synthetic or naturally derived.

Examples of Hair Styling Polymers Are:
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ®ES series available from ISP Corporation esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Further suitable anionic styling polymers include hydrophilic polyesters such as Eastman AQ-48 Ultra™, available from Eastman.

Amphoteric polymers can also be employed as hair styling polymers in the present invention. Examples include amphoteric hair styling polymers which can contain cationic groups derived from monomers such as t-butyl aminoethyl methacrylate as well as carboxyl groups derived from monomers such as acrylic acid or methacrylic acid. One specific example of an amphoteric hair styling polymer is Amphomer® (Octylacrylamide/acrylates/butylaminoethyl methacrylate copolymer) sold by the National Starch and Chemical Corporation.

Compositions of the Invention

Compositions of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like. Compositions of the invention comprise a cosmetically acceptable diluent or carrier. Preferably, the compositions are for use in styling human hair and, more preferably, they are packaged and labelled as such.

Preferably, the compositions of the invention comprise from 0.01% to 10% (preferably from 0.01% to 5%) by weight silicone, based on the total weight of the composition. A particularly preferred composition according to the invention is a hair spray composition comprising:
(i) from 0.01% to 10% (preferably from 0.1% to 10%) by weight of a hair styling polymer;
(ii) from 0.001% to 10% (preferably from 0.01% to 1%) by weight of a partially or fully fluorinated compound;
(iii) optionally, from 0.01% to 5% by weight of a silicone;
(iv) at least 20% (preferably al least 50%) by weight water; and
(v) up to 50% by weight of a propellant.

The carriers and additional components required to formulate cosmetic and personal care compositions of the invention vary with product type and can be routinely chosen by one skilled in the art. The following is a description of some of these carriers and additional components.

Carriers

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, by weight of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular composition to be used, and on whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular composition being used, with water, the $C_1$–$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions. Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses, the carrier can include a wide variety of conditioning materials. Where the hair care compositions are shampoos, the carrier can include, for example, surfactants, suspending agents, and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclcmethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

The compositions of the present invention preferably comprise, amongst other carriers, water and ethanol, with the amount of water being preferably at least 20% by weight of the composition, more preferably at least 40% by weight (such as at least 50% by weight), more preferably at least 60% by weight, more preferably at least 70% by weight, even more preferably at least 80% by weight of the composition. The weight ratio of water to organic solvent (including, for example, ethanol) may preferably vary from 1:4 to 10:1, more preferably 1:1 to 10:1, most preferably 2:1 to 10:1. The compositions may, alternatively, contain water as the only solvent ie, have a VOC of 0%.

Additional Components

A wide variety of additional components can be employed in cosmetic and personal care compositions according to the present invention. Examples include the following:

nonionic hair styling polymers such as, for example, homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

cationic hair styling polymers such as, for example, copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:

copolymers of N-vinylpyrrolidone and dimethylaminoethyl methacrylate, available from ISP Corporation as Copolymer 845, Copolymer 937 and Copolymer 958;

copolymers of N-vinylpyrrolidone and dimethylaminopropylacrylamide or methacrylamide, available from ISP Corporation as Styleze® CC10;

copolymers of N-vinylpyrrolidine and dimethylaminoethyl methacrylate;

copolymers of vinylcaprolactam, N-vinylpyrrolidone and dimethylaminoethylmethacrylate;

Polyquaternium-4 (a copolymer of diallyldimonium chloride and hydroxyethylcellulose);

Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, FC 905 and HM-552;

Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

- a perfume or fragrance, for example in an amount of from 0.01% to 1% by weight of the total composition.
- sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
- anti-dandruff actives such as zinc pyrithione, piroctone olamine, selenium disulphide, sulphur, coal tar, and the like.
- hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.
- surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.
- carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon—carbon double bonds and derived from a polyhydric alcohol. Examples of carboxylic acid polymer thickeners useful herein are those selected from the group consisting of carbomers, acrylates/C10–C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.
- emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.
- vitamins and derivatives thereof (e.g., ascorbic acid, vitamin E, tocopheryl acetate, retinoic acid, retinol, retinoids, and the like).
- cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).
- preservatives, antioxidants, chelators and sequestrants; and aesthetic components such as fragrances, colourings, hair nutrients and essential oils.

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macro-grafted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

The following non-limiting Examples further illustrate the preferred embodiments of the invention. All percentages referred to are by weight based on total weight unless otherwise indicated.

EXAMPLES

Method for Determining Bond Strengths

For an indication of the level of hold offered by a styling polymer and to assess whether or not it adheres to hair, the bond strength between the polymer and a single fibre is measured using an automated bond strength kit. The technique is based on the principle of using an automated bond strength kit to measure the force in grams to break a bond between a polymer and two perpendicularly crossed hair fibres. This was designed by Diastron Limited (Andover, UK) and is widely used in the hair styling industry.

Apparatus

Diastron model 600 fitted with Lacquer testing carousel controlled by Series MTTWin control software (Supplied by Diastron Ltd Andover UK).

Procedure a) Preparation of Hair Fibres

Spanish hair (Supplied by Hugo Royer Sandhurst UK) having a maximum and minimum diameter of between 60 and 80 microns is first cleaned by submersion in ether for 1 minute. It is then washed with a base shampoo (16% SLES 2EO) and air dried in a straight conformation at 25 deg C./50% RH for 12 hours.

b) Preparation of Styling Polymer Solution

Make up a 3% concentrated solution of the test styling polymer in a 55% water/45% ethanol mixture.

c) Diastron Control Software Parameters

The values for the test parameters within the MTTWin control panel (Lacquer Testing Routine) are set as follows:

| | |
|---|---|
| Percentage Extension % = | 100 |
| Rate mm/min = | 10 |
| Max Force gmf = | 200 |
| Gauge Force gmf = | 2 |
| Enable Break detection = | 20 |
| Carousel Set Up = | 25 samples, Start at 1 |
| (Analysis Break detection = | 5) | d) Protocol
1. Mount the cross hair fibres on the aluminium blocks provided using an alpha cyanoacrylate adhesive (e.g. Cyanolit™).
2. Locate the mounted aluminium blocks in the slots within the lacquer testing carousel.
3. Using the Diastron crimping apparatus and mounting block, attach brass ferrule at each end of 25 hair samples at a spacing of 30 mm as determined by the mounting block.
4. Lay the crimped samples across the mounted hair fibres so that they lie perpendicularly to each other.
5. Cut the crimped hair fibre using a sharp blade, above the cross-over point with the horizontal fibre, and at the end nearest to the centre of the carousel.
6. Using a 1 microliter syringe (Supplied by SGE International Pty Ltd) deposit 1 microliter of the 3% solids solution of the test styling polymer into the fibre crossover.
7. Allow to dry for 3 hours under required temperature and humidity conditions ie, the conditions under which the bond strength measurement is to be carried out.
8. Execute the automatic testing method using the parameters set previously.

e) Data Handling 25 separate load displacement plots are recorded for the carousel of samples. The peak load supported by the bond is recorded for each separate test and the mean load and standard deviation calculated for the carousel.

Examples 1 to 4

The bond strengths of two common styling resins neutralised with fluoroamines were measured under high humidity conditions (20° C., 80% RH) by the method detailed above.

The styling resins used were Amphomer 28-4910 (available from National Starch and Chemicals Company) and Luviset PUR (available from BASE).

Samples of these two polymers were neutralised separately with the fluoroamine 4-(trifluoromethyl)aniline (TFMA).

For comparison, a typical neutralising base such as 2-amino-2-methyl-1-propanol (AMP) was selected as a control. The neutralisation level in all experiments was fixed at 95%.

In Examples 1 to 3, Amphomer 28-4910 was neutralised with a specified fluoroamine. In the control, the performance of the fluoroamine neutralised polymer film was compared against an AMP neutralised Amphomer 28-4910.

In Example 4, Luviset PUR was neutralised with a combination of TFMA and AMP (50:50). This is compared with a Luviset PUR that was neutralised only with AMP in the control.

The bond strength data of the three fluoroamine neutralised Amphomer 28-4910 samples together with the control, at 20° C. and 80% RH, are given in Table 1 below.

TABLE 1

Bond strength data of three fluoroamines and AMP (control) neutralised Amphomer 28-4910.

| EXAMPLE | BASE | BOND STRENGTH (standard deviation) | FAILURE MECHANISM |
|---|---|---|---|
| 1 | TFMA | 36 g (±15) | Slight fracture and adhesive. |
| 2 | TFTFMA | 4 g (±1.1) | Very brittle dries as white deposit |
| 3 | TFEA | 0 g | Very brittle dries as white deposit |
| CONTROL | AMP | 33 g (±18) | Variety of adhesive and cohesive. |

The bond strength data presented in Table 1 indicate that TFMA neutralised Amphomer displays similar bond strength as that of AMP neutralised material. On the other hand, the bond strength of TFEA neutralised Amphomer 28-4910 was very poor zero bond strength).

The bond strength data of the fluoroamine and AMP neutralised Luviset PUR at 20° C. and 80% RH is shown in Table 2 below.

TABLE 2

Bond strength data of TFMA and AMP neutralised Luviset PUR

| EXAMPLE | BASE | BOND STRENGTH (STANDARD DEVIATION) | FAILURE MECHANISM |
|---|---|---|---|
| 4 | 50% AMP/ 50% TFMA | 36 g (±7) | Slightly ductile and cohesive |
| CONTROL | 100% AMP | 0 g | Very ductile |

The bond strength data presented in Table 1 indicates that TFMA neutralised Amphomer 28-4910 displays a similar bond strength to that of AMP neutralised material.

The bond strength data presented in Table 2 shows that the TFMA+AMP neutralised Luviset PUR performs well under very high humidity conditions (20° C., 80% RH). The adhesive bond strength of this polymer film was very high (36 g) under such severe and demanding conditions. On the other hand, the performance of the control (AMP neutralised) material was very poor (zero bond strength). Clearly the introduction of TFMA has a significant effect on the performance of the Luviset PUR polyurethane styling resin at 80% relative humidity (RH).

Formulation Examples for Fluoroamine Neutralised Styling Resins

The following are examples of compositions according to the invention.

The materials in the examples include the following:

| Material | Supplier | Function |
|---|---|---|
| Silicone emulsion X2 1787 ™ | Dow Corning | Conditioning |
| VOLPO CS 50 ™ | Croda | Surfactant |
| Sepicide LD ™ | Seppic | Preservative |
| Cremophor RH410 ™ | BASF | Stabiliser |
| Silicone DC 200/DC 24 S ™ | Dow Corning | Conditioning |
| Silwet L7602/L-720 ™ | Union Carbide | Surfactant |
| CAP 40 ™ | Calor Gas | Propellant |
| Carbopol 980 ™ | B F Goodrich | Structurant |
| Jaguar HP-105 ™ | Rhodia | Conditioning |
| Silicone Fluid 245 ™ | Dow Corning | Conditioning |
| Luviset PUR | BASF | Adhesive |
| AMP | Fluka | Neutraliser |
| TFMA | Fluka | Neutraliser |
| 2,3,5,6-tetrafluoro-4-(trifluoromethyl) aniline (TFTFMA) | Fluka | Neutraliser |
| 1,1,1-trifluoroethylamine (TFEA) | Fluka | Neutraliser |

Ethanol is SD Alcohol 40-B (92% active)

In the following examples Luviset PUR is neutralised to 95% with AMP and an equimolar amount of TFTFMA or TFMA and is denoted as Polymer 1. TFMA is used in Examples 5, 6, 9 and 10. TFTFMA is used in Examples 7 and 8.

Example 5

A styling mousse is formulated as follows:

| Material | % in product (w/w) |
|---|---|
| Silicone Emulsion X2 1787 | 1.2 |
| Polymer 1 | 1.5 |
| VOLPO CS 50 | 0.3 |
| Sepicide LD | 0.4 |
| Cremophor RH410 | 0.2 |
| Ethanol | 7.5 |
| CAP 40 | 8.0 |
| Perfume | 0.2 |
| Water | to 100% |

Example 6

A hairspray is formulated as follows:

| Material | % in product (w/w) |
|---|---|
| Polymer 1 | 3.0 |
| Silicone DC200 | 0.09 |
| Silwet L7602 | 0.09 |
| CAP 40 | 35.0 |
| Ethanol | 60.0 |
| Perfume | 0.10 |
| Water | to 100% |

Example 7

A pump spray is formulated as follows:

| Material | % w/w |
|---|---|
| Ethanol | 60.0 |
| Polymer 1 | 3.5 |
| Silwet L-720 | 0.3 |
| Silicone DC24S | 0.15 |
| Fragrance | 0.3 |
| Water | to 100% |

Example 8

A styling gel is formulated as follows:

| Material | % w/w |
|---|---|
| Polymer 1 | 3.8 |
| Carbopol 980 | 0.4 |
| Water | to 100% |
| Sepicide LD | 0.4 |
| Sodium hydroxide (8% 2M) | 0.1 |
| Ethanol | 10.0 |
| Cremaphor RH410 | 0.4 |
| Jaguar HP-105 | 0.2 |
| Perfume | 0.15 |

Example 9

A 55% voc propelled aerosol composition is formulated as follows:

| Material | % w/w |
|---|---|
| Polymer 1 | 3.75 |
| Silicone Fluid 245 | 0.20 |
| Fragrance | 0.32 |
| Ethanol | 19.53 |
| Dimethyl ether | 35.00 |
| Sodium benzoate | 0.26 |
| Cyclohexylamine | 0.21 |
| Water | to 100% |

Example 10

A 55% voc pump hairspray composition is formulated as follows:

| Material | % w/w |
|---|---|
| Polymer 1 | 3.75 |
| Cyclopentasiloxane (99% active) | 0.15 |
| Benzophenone 4 | 0.0001 |
| Fragrance | 0.25 |
| Ethanol | 58.00 |
| Water | to 100% |

What is claimed is:

1. A cosmetic or personal care composition comprising: a hair styling polymer having one or more groups selected from acidic functional groups, anionic groups derived from the acidic functional groups, or a mixture of said groups; a partially or fully fluorinated compound having the formula $RNR^1R^2$ in which $R^1$ and $R^2$ are H or an alky group having 1–12 carbon atoms, and R is a phenyl group substituted with one or more groups selected from the group consisting of fluorine, partially or fully fluorinated $C_1$ to $C_6$ alkyl, and their mixtures; and a cosmetically acceptable diluent or carrier.

2. A composition according to claim 1 in which the partially of fully fluorinated compound is selected from the group consisting of 2,3,5,6-tetrafluoro-4-(trifluoromethyl) aniline, 4-(trifluoromethyl)aniline and mixtures thereof.

3. A composition according to claim 1 further comprising a non-fluorinated amine.

4. A composition according to claim 3 in which the non-fluorinated amine is selected from the group consisting of: 2-amino-2-methyl-1,3-propanediol; 2-amino-2-ethyl-1, 3-propanediol; 2-amino-2-methyl-1-propanediol; 2-amino-1-butanol; monoethanolamine; diethanolamine; triethanolamine; monisopropanolamine; diisopropanolamine; triisopropanolamine; dimethylstearamine; and mixtures thereof.

5. A composition according to claim 1 in which the hair styling polymer comprises carboxylic acid groups and/or salts thereof.

6. A composition according to claim 1 further comprising an inorganic base.

7. A composition according to claim 6 in which the inorganic base is selected from the group consisting of sodium hydroxide, potassium hydroxide, ammonium hydroxide, borax and mixtures thereof.

8. A composition according to claim 4 in which the ratio of partially or fully fluorinated compound to non-fluorinated amine by weight is in the range of from 10:1 to 1:10.

9. A composition according to claim 6 in which the ratio of inorganic base to partially or fully fluorinated compound and non-fluorinated amine is in the range of from 100:1 to 1:100.

10. A composition according to claim 1 in which the degree of neutralization of the hair styling polymer is in the range of from 10 to 100%.

11. A composition according to claim 1 in which the hair styling polymer is present in an amount of from 0.01 to 10% by weight.

12. A composition according to claim 1 in which the partially or fully fluorinated compound is present in an amount of from 0.001 to 10% by weight.

13. A composition according to claim 1 which further comprises silicone in an amount of from 0.01% to 10% by weight.

14. A composition according to claim 1 in which the cosmetically acceptable diluent or carrier comprises ethanol and/or water.

15. The composition according to claim 14 in which the composition comprises at least 40% by weight water.

16. A composition according to claim 1 which is packaged in the form of a non-aerosol pump spray.

17. A composition according to claim 1 which is a hair styling composition.

18. A composition according to claim 2 in which the fluorinated compound is 2,3,5,6-tetrafluoro-4-(trifluoromethyl)aniline.

* * * * *